United States Patent
Amontov et al.

(10) Patent No.: US 7,070,922 B2
(45) Date of Patent: Jul. 4, 2006

(54) SURFACE TREATMENT

(75) Inventors: Sergey Amontov, Gattikon (CH);
Bruno Michel, Adliswil (CH); Sally Ann Swanson, San Jose, CA (US);
Heiko Wolf, Pfaeffikon (CH)

(73) Assignee: International Business Machines Corporation, Armonk, NY (US)

( * ) Notice: Subject to any disclaimer, the term of this patent is extended or adjusted under 35 U.S.C. 154(b) by 87 days.

(21) Appl. No.: 10/309,674

(22) Filed: Dec. 4, 2002

(65) Prior Publication Data

US 2004/0110276 A1      Jun. 10, 2004

(51) Int. Cl.
*C12Q 1/00*    (2006.01)
*C12Q 1/68*    (2006.01)

(52) U.S. Cl. ............................... 435/4; 435/6; 435/7.1; 435/287.2

(58) Field of Classification Search .................... 435/6, 435/7.9, 287.2; 536/24.3, 24.33
See application file for complete search history.

(56) References Cited

U.S. PATENT DOCUMENTS

| | | | | |
|---|---|---|---|---|
| 4,812,512 | A | * | 3/1989 | Buendia et al. .......... 525/54.11 |
| 5,510,481 | A | * | 4/1996 | Bednarski et al. .......... 536/120 |
| 6,413,934 | B1 | * | 7/2002 | Stayton et al. ................ 514/12 |
| 2002/0028455 | A1 | * | 3/2002 | Laibinis et al. ................ 435/6 |
| 2002/0045277 | A1 | | 4/2002 | Schmid et al. |
| 2003/0017508 | A1 | * | 1/2003 | Charych et al. ............. 435/7.9 |

FOREIGN PATENT DOCUMENTS

| | | |
|---|---|---|
| EP | 1 132 739 | 9/2001 |
| GB | 2324866 | 11/1998 |
| WO | WO 99/17120 | 4/1999 |

OTHER PUBLICATIONS

Beier, et al., "Versatile derivatisation of solid support media for covalent bonding on DNA-microchips," Nucleic Acids Research, 1999, 27(9), 1970-1977.
Chrisey, et al., "Covalent attachment of synthetic DNA to self-assembled monolayer films," Nucleic Acids Research, 1996, 24(15), 3031-3039.
Zalipsky, S., "Functionalized Poly(ethylene glycol) for Preparation of Biologically Relevant Conjugates," Bioconjugate Chem, 1995, 6, 150-165.
Copy of PCT Search Report dated Jul. 17, 2004 from corresponding PCT application, PCT/US03/38752.

* cited by examiner

*Primary Examiner*—Jeffrey Fredman
(74) *Attorney, Agent, or Firm*—Kin-Wah Tong, Esq.; Wan Yee Cheung, Esq.; Patterson & Sheridan, LLP

(57) ABSTRACT

Described is a process for producing a biomolecular monolayer on a biosensor surface comprising the steps of: reacting a biosensor surface with a solution of heterobifunctional reagent having a first functional group and a second functional group, the first functional group being capable of forming a covalent bond to the biosensor surface groups, the second functional group forming a covalent bond with a homobifunctional polymer to obtain a self-assembled monolayer, and thereafter reacting the monolayer with capture molecules.

2 Claims, 6 Drawing Sheets

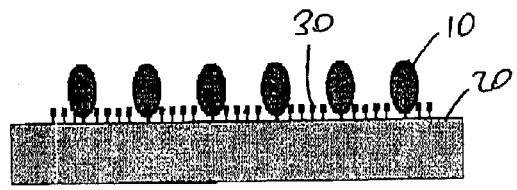
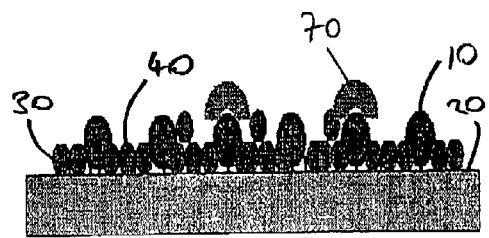
FIG.1A	FIG.1B
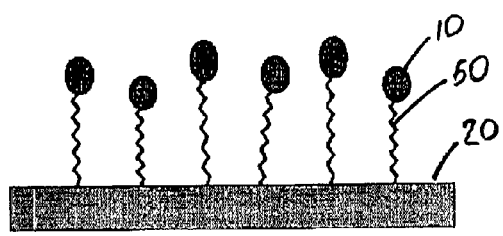
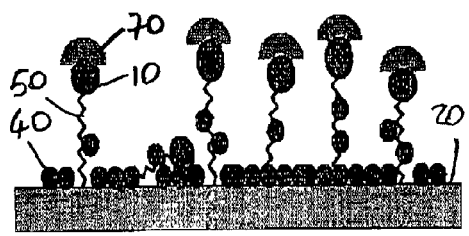
FIG.1C	FIG.1D
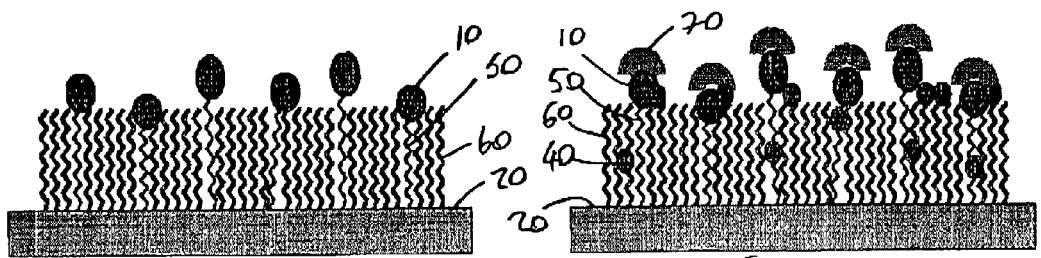
FIG.1E	FIG.1F
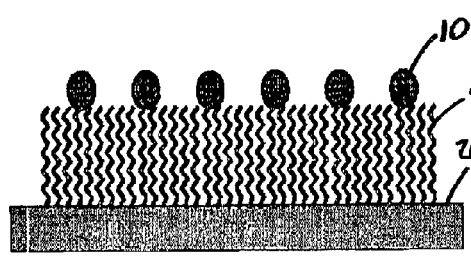
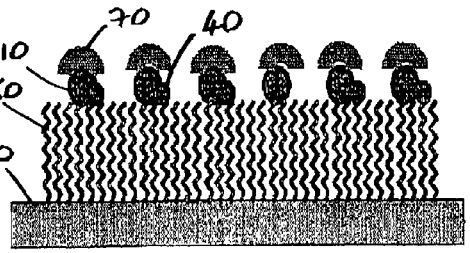
FIG.1G	FIG.1H

SURFACE TREATMENT

BACKGROUND OF THE INVENTION

1. Field of the Invention

The present invention generally relates to surface treatment and particularly relates to methods and apparatus for treating surfaces such as biosensor surfaces by molecular chemisorption.

2. Discussion of Related Art

Production of biosensor arrays typically involves patterned deposition of biomolecules onto a surface. Sensitivity, reproducibility, and selectivity are significant aspects of biosensor quality. Sensitivity is typically achieved via a dense layer of chemisorbed capture molecules to efficiently capture target molecules. Reproducibility typically depends on highly reproducible anchoring chemistry and good quality patterning of capture molecules. Selectivity typically depends on high selectivity of target molecules and low non-selective adsorption of other molecules. The latter can limit utility of biosensors by accounting for 30% of the signal to be detected.

Bioconjugation involves linking molecules to form a complex having the combined properties of the individual components. Natural and synthetic compounds, and their activities, can be chemically combined to engineer substances having desired characteristics. For example, a protein bound to a target molecule in a complex mixture may be cross-linked with another molecule capable of being detected to form a traceable conjugate. The detection component provides visibility of the target component to produce a complex that can be localized, followed through various processes, or used for measurement.

Bioconjugation has affected many areas in the life sciences. Application of cross-linking reactions to creation of novel conjugates with particular activities has enabled the assay of minute quantities of substances for detection of cellular components and treatment of disease. The ability to chemically attach one molecule to another has produced a growing industry serving research, diagnostics, and therapeutic markets. A significant portion of biological assays is now performed using conjugates for interaction with specific analytes in solutions, cells, or tissues. An overview of conjugate molecules, reagent systems, and applications of bioconjugate techniques is given in G. T. Hermanson, *"Bioconjugate Techniques"*, Academic Press, San Diego, 1996.

Surfaces for use in biological environments are found in tools for molecular and cell biology such as substrates for Enzyme Linked Inmmunosorbent Assay (ELISA) in cell cultures, contact lenses, implanted prostheses, catheters, and containers for storage of proteins. Many such surfaces are quickly coated with a layer of proteins via spontaneous adsorption. Some have a beneficial effect. Others are detrimental. There is much interest in identifying biologically "inert" materials for resisting adsorption of proteins. A conventional surface treatment method for introducing such resistance involves coating the surface with poly(ethylene glycol) (PEG). See, for example J. M. Harris ed. *Poly(ethylene glycol) Chemistry: Biotechnical and Biomedical Applications*, Plenum, New York, 1992. Further details of PEG are provided in Gombotz, W. R. et al., *J. Biomed. Matter. Res.* 15, 1547–1562 (1991). An alternative approach involves the pre-adsorption of bovine serum albumin. This approach however suffers from denaturation of the protein over time or exchange of the protein with other molecules. Therefore, this approach is unsuitable for application to biosensors for detecting presence of proteins by mass or primary amines. Self-assembled monolayers of short chain PEG oligomers (n=2–7) have also been shown to resist adsorption of proteins. See, for example Mrksich, M. and Whitesides, G. M., *Annu. Rev. Biophys. Biomol. Struct.* 25, 55–78 (1996). However, a protein attempting to adsorb may compress and desolvate PEG. These effects are both energetically disadvantageous. See, for example Jeon, S. I. and Andrade, J. D. *"Protein surface interactions in the presence of polyethylene oxide: effect of protein size"*, J. Coll. Interface Sci. 142, 159–166 (1991); and, Jeon, S. I., Lee, J. H., Adrade, J. D. and de Gennes, P. G., *"Protein surface interactions in the presence of polyethyleneoxide: simplified theory"*, J. Coll. Interface Sci. 142, 149–158 (1991)).

Biosensor surfaces are typically formed from borosilicate glass. Various conventional schemes for attaching capture molecules, such as antibodies or DNA oligomers, to a biosensor surface will now be described.

Referring to FIG. 1A, in one conventional scheme, direct chemisorption or physisorption binds capture molecules 10 to the surface 20. The surface 20 is functionalized with relatively short linker molecules 30. For example, the surface 20 may be amine-functionalized. The linkers 30 immobilize the capture molecules 10 on the surface 20. Unwanted molecules also present on the surface 20 can be typically removed by stringent washing to optimize selectivity of the biosensor. However, washing can remove physisorbed molecules. Chemisorbed molecules are more resistant to washing. Referring to FIG. 1B, this scheme leaves many linkers 30 exposed. This leads to much nonspecific chemisorption or physisorption of other molecules 40. This reduces the selectivity of the biosensor. The ratio of molecules bound by specific interaction to molecules bound by nonspecific interaction is reduced. Although the selectivity of the capture molecules 10 may be high in solution, many detection methods are convoluted by presence of other molecules 40. Additionally, direct physisorption or chemisorption of the capture molecules 10 limits molecular mobility. Few capture molecules 10 have full functionality. The sensitivity of the capture molecules 10 is thus reduced. Binding efficiency is usually reduced where the capture molecules 10 are for binding assays. The affinity constant and binding kinetics vary in dependence on the orientation of chemisorption. This results in less target molecules 70 such as antigens being bound to the surface 20. Also, there is higher binding variability between different surfaces. If the detection scheme employed cannot distinguish between the target molecules 70 and the other molecules 40, the effective specificity of the biosensor is significantly reduced. This is common in both label free and labelled detection schemes. Stringent washing does not usually correct this problem because cooperative effects during nonspecific binding are virtually irreversible.

Referring to FIG. 1C, in another conventional scheme, the capture molecules 10 are chemisorbed to the surface 20 through spacer molecules 50. As indicated earlier, chemisorption of capture molecules 10 allows more stringent washing procedures, thus reducing nonspecifically physisorbed molecules. The spacers 50 are longer than the linkers 30 herein before described with reference to FIG. 1A. The spacers 50 tether the capture molecules 10 to the surface 20. However, the spacers 50 also allow limited movement of the capture molecules 10 relative to the surface 20. This allows the capture molecules 10 increased activity. The mobility and thus functionality of capture molecules 10 is improved. Binding efficiency of the capture molecules 10 chemisorbed through spacers 50 is thus increased. However, referring to FIG. 1D, the exposed surface 20 and the spacers 50 allow nonspecific binding of other molecules 40. Nonspecific binding can occur in roughly the same amount as in the FIG. 1B arrangement.

Referring to FIG. 1E, in a modification of the FIG. 1C scheme, the capture molecules 10 anchored to the surface 20 through spacers 50 in a sea of biocompatible molecules 60. The biocompatible molecules 60 are resistant to nonspecific adsorption of the other molecules 40. This improves the effective specificity of the surface 20. Referring to FIG. 1F, nonspecific binding is reduced because the surface 20 is less exposed. Only the spacers 50 and the capture molecules 10 offer sites for nonspecific binding of other molecules 40. Stringent washing can improve specificity further by removing more nonspecifically bound molecules 40 than specifically bound molecules 10.

The susceptibility of biosensors to nonspecific adsorption also depends on labeling and detection schemes employed. For example, sandwich ELISA assays are less susceptible because the signal measured depends only on the number of target antigen molecules 10 and the specificity with which labeling antibodies bind to the surface 20. This approach is inert because it involves a dual selective detection. However, label-free detection schemes are more susceptible to other molecules 40 adsorbing nonspecifically to the surface 20. These schemes measure the protein/DNA present on the surface 20 by mass or refractive index. More control over nonspecific adsorption is needed than in sandwich ELISA biosensors. Control over nonspecific adsorption and nonspecific signal generation is also important where bound molecules are detected by chemical labeling techniques. Such control is particularly desirable when chemical labeling exhibits cross-reactivity with chemical groups involved in the chemisorption. A barrier can be added to prevent access to the groups. However, BSA blocking of nonspecific adsorption is not usually possible because BSA produces a signal and reduces the "effective" selectivity of the biosensor.

Nucleic acid aptamers are useful for biosensor production because they can form three dimensional structures. Aptamers can also bind a range of target molecules with acceptable affinity and specificity. Also, aptamers can function in a similar manner to protein molecules. For example, aptamers can change in structure due to ligand-binding. There are many different receptors that are useful in biosensor arrays. However, aptamers are especially useful for several reasons. One reason is that aptamers can be more easily engineered than antibodies. Following selection, aptamers can be reduced to 30–60 nucleotide residue core sequences without reducing binding function. Another reason is that modifications such as fluorescent reporters can be easily introduced by chemical synthesis. Yet another reason is that aptamer structure is mainly a function of Watson-Crick base pairing. Secondary structural interactions allow aptamers to be more easily converted to receptors than antibodies.

Referring to FIG. 2A, in a conventional process for producing a biosensor as herein before described with reference to FIG. 1F, capture molecules in the form of amine-functionalized aptamers 120 are crosslinked onto a glass surface 20. The surface is first functionalized with APTS (3-aminopropyl triethoxysilane) 100. The cross-linking is then performed by spacers in the form of bifunctional succinimide crosslinkers (BS3) 110.

Following such chemisorption of capture molecules 10, the remaining crosslinking spacers 50 and amine surface 20 are blocked with a single functionalized succinimide to cover the amines, and ethanolamine to saturate unreacted succinimide groups. Any remaining surface areas may be treated with PEG. These post-chemisorption steps reduce nonspecific protein absorption. However, as herein before indicated, spaces between the capture molecules 10 and the spacers 50 can still react. These spaces accept nonspecific protein adsorption. BS3 spacers are too short for many proteins and pose problems as herein before described with reference to FIG. 1A. In addition, the functionalizing, cross-linking, and blocking steps each involve exposure of the surface 20 to a different environment in a different bath. This process is laborious, time consuming, and wasteful of raw materials.

It would be desirable to provide a method for effecting chemisorption of capture molecules with improved activity, accessibility, capacity, and specificity of the capture molecules. In particular, it would be desirable to provide a method for biosensor fabrication that: irreversibly attaches capture molecules to the biosensor surface; provides sufficient mobility and accessibility for capture molecules to remain functional; and, minimizes nonspecific adsorption of target antigens or other molecules. It would also be desirable to provide a method for fabricating biosensors which is less laborious, less time consuming, and less wasteful of materials.

SUMMARY OF THE INVENTION

In accordance with the present invention, there is now provided a process for producing a biomolecular monolayer on a surface comprising the steps of: reacting the surface with a solution of a heterobifunctional reagent having a first functional group and a second functional group, the first functional group being capable of forming a covalent bond to surface groups, the second functional group forming a covalent bond with a homobifunctional polymer to obtain a self-assembled monolayer, and thereafter reacting the monolayer with biomolecules.

The term biomolecules, as used herein, refers to molecules having biological functionality. For example, the biomolecules may be amine-functionalised. Equally, the biomolecules may comprise a nucleic acid aptamer derivative. Preferably, an excess of the homobifunctional polymer is involved. The heterobifunctional reagent is preferably mixed with the homobifunctional polymer prior to exposure to the surface. The surface may be glass, metal, or the like. The heterobifunctional reagent is preferably an aminoalkyl trialkoxysilane. In a preferred embodiment of the present invention, the heterobifunctional reagent is 3-aminopropyl triethoxysilane. However, the heterobifunctional reagent may be an alkylthiol. The second functional group of the heterobifunctional reagent preferably reacts with one functional group of the homobifunctional polymer to form a covalent bond therebetween. In a preferred embodiment of the present invention, the functional groups of the homobifunctionl polymer are N-hydroxy succinimide groups. The homobifunctional polymer may be a homobifunctional polyethylene glycol. The biomolecules may react with one functional group of the homobifunctional polymer to form a covalent bond therebetween. The covalent bonds formed between the biomolecules and the homobifunctional polymer is preferably an amide bond.

Viewing the present invention from another aspect, there is now provided a biosensor having a surface layer formed by a process for producing a biomolecular monolayer on a surface comprising the steps of: reacting the surface with a solution of a heterobifunctional reagent having a first functional group and a second functional group, the first functional group being capable of forming a covalent bond to surface groups, the second functional group forming a covalent bond with a homobifunctional polymer to obtain a self-assembled monolayer, and thereafter reacting the monolayer with capture molecules.

Viewing the present invention from yet another aspect, there is now provided a biosensor array comprising a patterned deposit of biomolecules on a substrate wherein the patterned deposit is formed by a process for producing a biomolecular monolayer on a surface comprising the steps of: reacting the surface with a solution of a heterobifunctional reagent having a first functional group and a second functional group, the first functional group being capable of forming a covalent bond to surface groups, the second functional group forming a covalent bond with a homobifunctional polymer to obtain a self-assembled monolayer, and thereafter reacting the monolayer with capture molecules.

Viewing the present invention from a further aspect, there is now provided a biochip having a surface layer formed by a process for producing a biomolecular monolayer on a surface comprising the steps of: reacting the surface with a solution of a heterobifunctional reagent having a first functional group and a second functional group, the first functional group being capable of forming a covalent bond to surface groups, the second functional group forming a covalent bond with a homobifunctional polymer to obtain a self-assembled monolayer, and thereafter reacting the monolayer with biomolecules.

Viewing the present invention from still a further aspect, there is now provided a biochip array comprising a patterned deposit of biomolecules on a substrate wherein the patterned deposit is formed by a process for producing a biomolecular monolayer on a surface comprising the steps of: reacting the surface with a solution of a heterobifunctional reagent having a first functional group and a second functional group, the first functional group being capable of forming a covalent bond to surface groups, the second functional group forming a covalent bond with a homobifunctional polymer to obtain a self-assembled monolayer, and thereafter reacting the monolayer with biomolecules.

In a preferred embodiment of the present invention, there is provided a simple two step chemical process for attaching capture molecules to a biosensor surface. The process employs a homobifunctional PEG crosslinker with succinimide groups at each end to chemisorb the capture molecules onto the surface with higher density and reproducibility than hitherto possible. The process improves the sensitivity and selectivity of bioassays. Also provided are protocols and devices for treating biosensor surfaces economically with high yield.

In a particularly preferred embodiment of the present invention, there is provided a method for attaching a spacer molecule to a clean glass surface. The method involves a non-symmetrical reaction of a heterobifunctional reagent such as 3-aminopropyl triethoxysilane (APTS) with a homobifunctional polymer such as homobifunctional succinimide end functionalized PEG polymer. The reaction is carried out in a water free solvent. A high concentration is employed to favor bimolecular reactions. The present invention also extends a device for applying a small amount of prereacted reagent to glass surfaces in the interests of saving expensive reagents.

BRIEF DESCRIPTION OF THE DRAWINGS

Preferred embodiments of the present invention will now be described, by way of example only, with reference to the accompanying drawings, in which:

FIG. 1A is a cross sectional view of a biosensor surface showing direct adsorption of capture molecules on a surface;

FIG. 1B is a cross sectional view of the surface showing nonspecific chemisorption of other molecules to the arrangement shown in FIG. 1A;

FIG. 1C is a cross sectional view of the surface showing chemisorption of capture molecules via spacer molecules;

FIG. 1D is a cross sectional view of the surface showing nonspecific chemisorption of other molecules to the arrangement shown in FIG. 1C;

FIG. 1E is a cross sectional view of the surface showing capture molecules anchored to a surface via spacer molecules in a sea of biocompatible molecules;

FIG. 1F is a cross sectional view of the surface showing nonspecific chemisorption of other molecules to the arrangement shown in FIG. 1E;

FIG. 1G is a cross sectional view of a preferred embodiment of the present invention in which capture molecules are anchored to a surface through combined anchor/spacers;

FIG. 1H is a cross sectional view showing nonspecific chemisorption of other molecules to the arrangement shown in FIG. 1G;

DETAILED DESCRIPTION OF THE PREFERRED EMBODIMENT

Figure 2A:
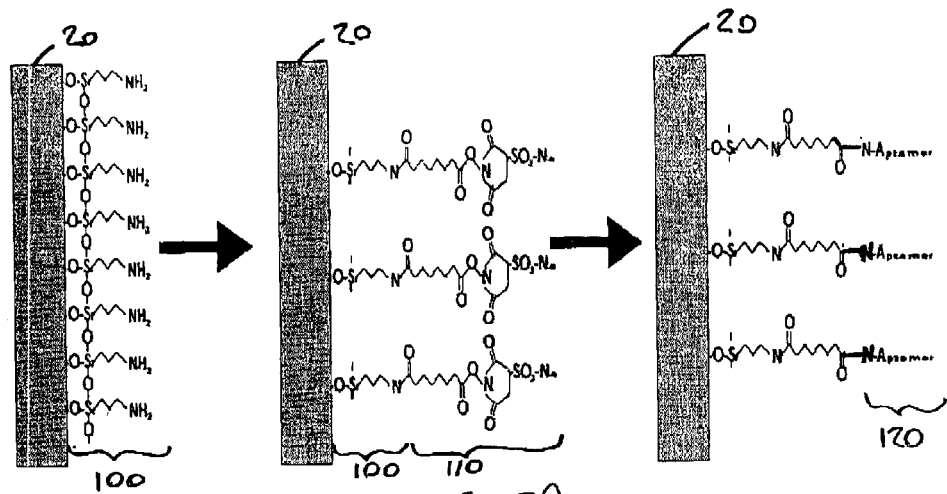
FIG. 2A is a flow diagram showing attachment of an amine-functionalized aptamer to an APTS (3-aminopropyl triethoxysilane) functionalized glass surface via a bifunctional succinimide crosslinker (BS3)

With reference to FIG. 1G, in a preferred embodiment of the present invention, there is provided a biosensor in which capture molecules 10 are anchored to a glass biosensor surface 20 via combined anchor/spacers acting as biocompatibility molecules 80.

Referring now to FIG. 1H, the biocompatiblity molecules 80 are resistant to the nonspecific adsorption of other molecules 40 and also act as crosslinkers. This further reduces potential nonspecific adsorption sites. Advantageously, surplus biocompatibility molecules 80 provide lateral spacing of capture molecules 40 without leaving the underlying surface 20 exposed. The concentration of capture molecules 10 applied determines the density of surface activation. In operation, target molecules 70 are bound to the surface 20 via the capture molecules 80.

Figure 2B:
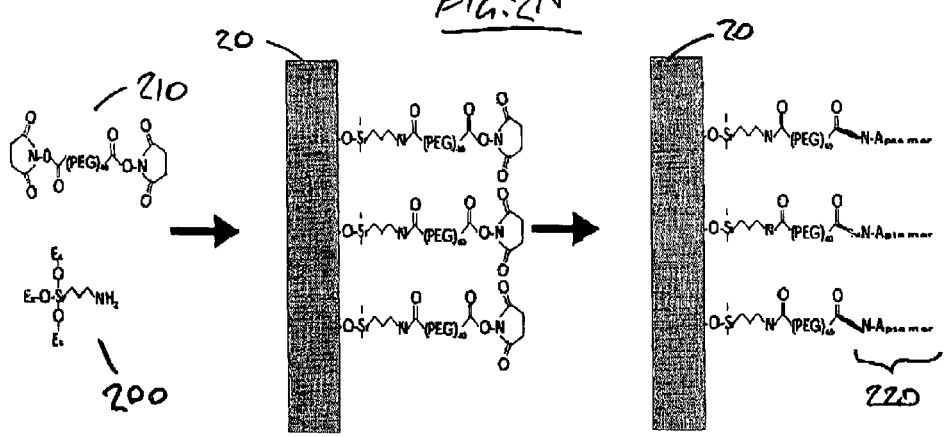
FIG. 2B is a flow diagram showing attachment of an amine-functionalized aptamer to a glass surface where the surface is treated with a preprocessed solution of APTS (aminopropyltrimethoxysilane) and a homobifunctional PEG N-hydroxy succinimide crosslinker (NHS) in DMSO.
Figure 2C:
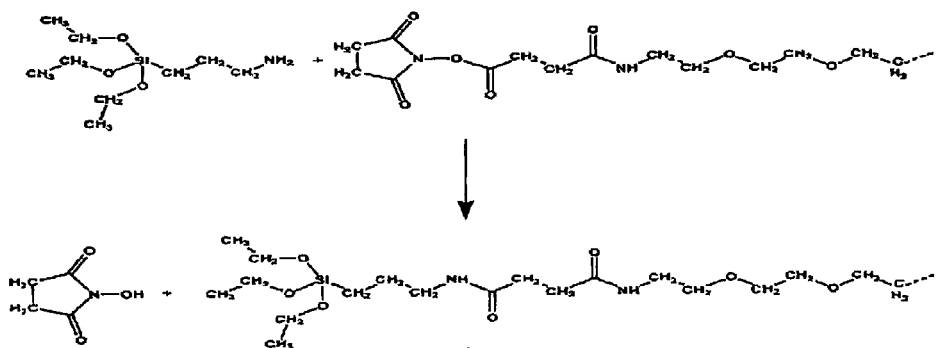
FIG. 2C shows a reaction of APTS (aminopropyl trimethoxysilane) to one end of a homobifunctional PEG N-hydroxy succinimide crosslinker (NHS) in DMSO.

Referring to FIGS. 2B and 2C in combination, in a particularly preferred embodiment of the present invention, the glass surface 20 is treated with a preprocessed solution of APTS (aminopropyl trimethoxysilane) 200 and a homobifunctional PEG N-hydroxy succinimide crosslinker (NHS) 210 in dimethyl sulphoxide (DMSO). The NHS crosslinker 210 has two NHS functions; one at each end. At one end, the first NHS function binds to the APTS 200. At the other end, the second NHS function binds to an amine-functionalized aptamer 220. In both case, the binding is via covalent bonds.

Figure 3:
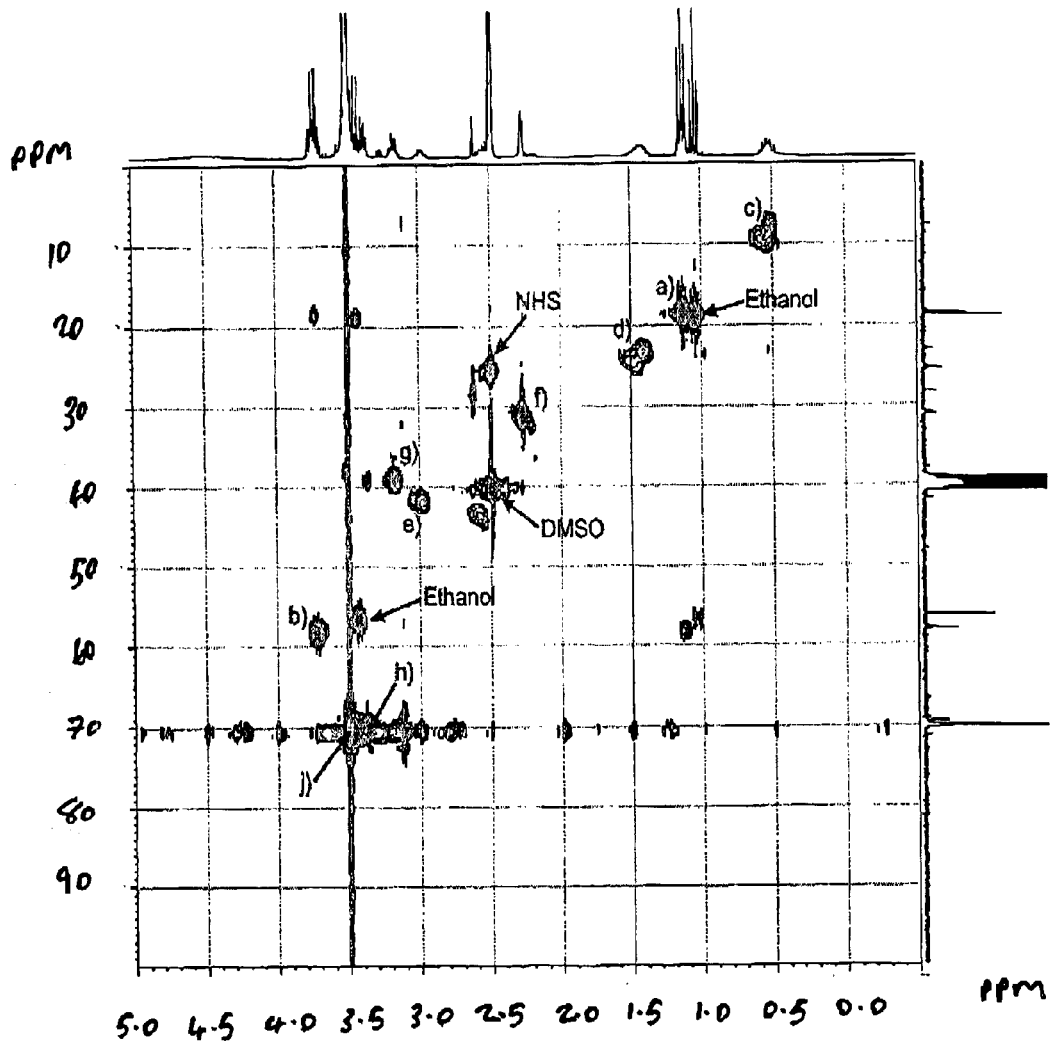
FIG. 3 is an NMR spectrum showing reaction of aminopropyl triethoxysilane with NHS PEG.
Figure 3:
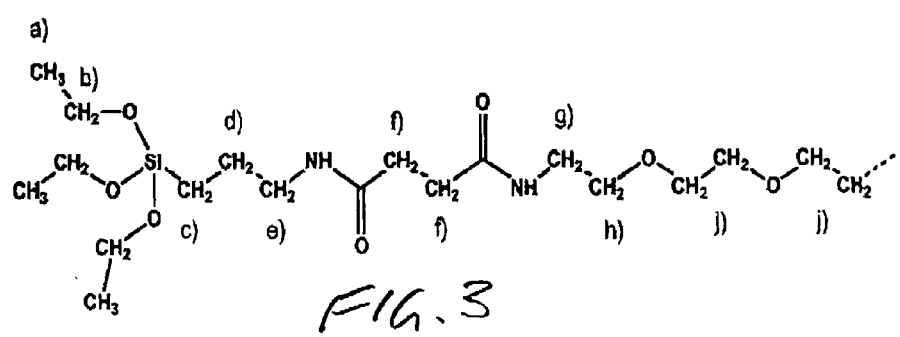

FIG. 3 shows an NMR spectrum illustrating the reaction of the APTS 200 with the NHS PEG 210. The molecule shown is the result of that reaction.

In a particularly preferred process embodying the present invention, the reaction referred to in connection with FIG. 3 starts with preparation of a heterobifunctional reagent in the form of NHS-PEG-triethoxysilane from APTS and a homobifunctional PEG in the form of (a,w)NHS-PEG 2000, Rapp Polymere in a solution of DMSO at 42–48 degrees C. 300 microliters of 80 mM homobifunctional NHS-PEG in DMSO is mixed with 200 microliters of 120 mM APTS in DMSO, 6 microliters APTS in 300 microliters DMSO. This produces an equimolar mixture with both substances having a concentration of 48 mM. The mixture is heated to between 46 and 50 degrees C. and allowed to react for between 30 and 60 minutes. The result is then transferred to a narrow gap between two pretreated glass surfaces for between 60 and 120 minutes. Capillary action is employed to promote ingress of the mixture into the gap until the gap is filled. Filling the gap at elevated temperature is desirable. Otherwise, the viscosity of the mixture is too high. The surfaces were pretreated by a mixture of 1 part concentrated sulfuric (Fluka) acid and 2 parts hydrogen peroxide (Fluka puriss) for several hours and then washed in deionized water. The mixture of sulfuric acid and hydrogen peroxide, sometimes called 'piranha solution', heats to boiling point during mixing.

Remaining with FIG. 3, NMR performed after 30 minutes shows that over 90% amine groups react with the NHS groups on the PEG and that no free APTS can be detected with a detection threshold of 10%. Homobifunctional side products of unreacted NHS-PEG and homobifunctional triethoxysilane PEG form statistically. However, these do not disturb chemisorption. This is because NHS-PEG cannot chemisorb to glass. Homobifunctional triethoxysilane PEG may only dilute the density of the NHS-PEG and will decay to Si—(OH)3 in the subsequent protein adsorption step.

Figure 4A:
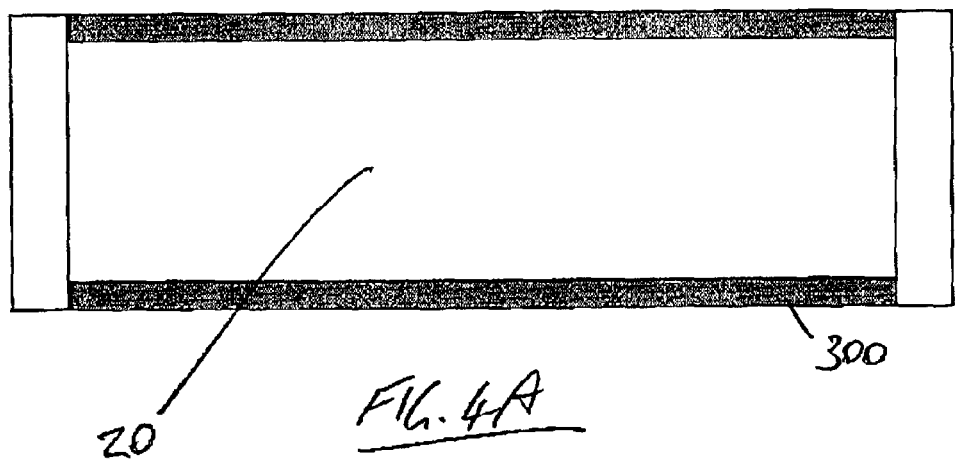
FIG. 4A is a plan view of a fluid cell for treating biosensor surfaces.
Figure 4B:
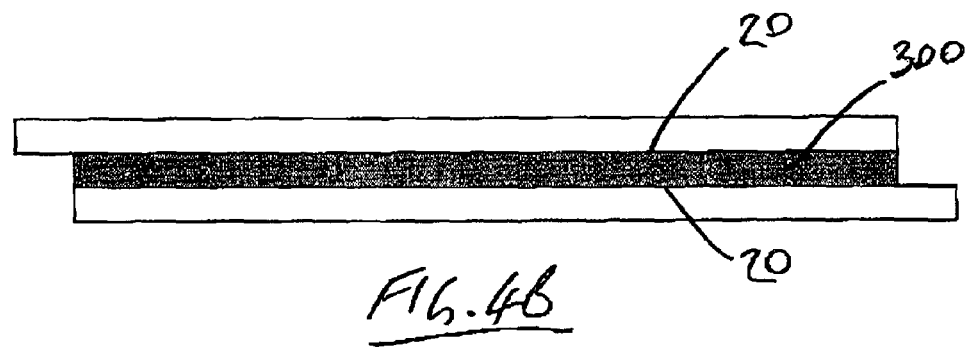
FIG. 4B is a side view of the fluid cell.
Figure 4C:
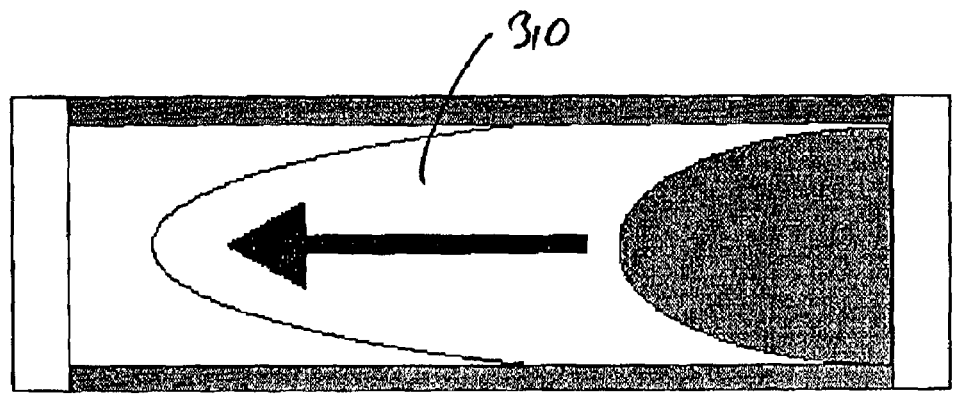
FIG. 4C is another plan view of the cell.

FIGS. 4A to C show a fluid cell for treating glass surfaces 20 with a high concentration of a relatively expensive linker/spacer biocompatibility molecule such as that herein before described. Referring to FIGS. 4A and 4B, the surfaces 20 are separated and sealed by a 100–300 micrometers thick peripheral gasket 300. The gasket 300 may be formed from Teflon. Referring to FIG. 4C, the fluid cell is then filled with the reactive mixture by capillary force from one side with a volume of 150 microliters. Specifically, the mixture is drawn into the gap intervening between the surfaces 20 and defined by the gasket 300 via capillary action. The surfaces 20 are thus treated.

The technique herein before described is superior to conventional techniques because the heterobifunctional reagent is prepared in situ. No further purification is needed. This is especially advantageous because purification of silanized PEG by conventional techniques such as chromatography is very difficult if not impossible. Non-aqueous conditions prevent polymerization of APTS and facilitate regular treatment of the surfaces 20. In-situ preparation of the reagent provides a fresh reactive intermediate which is not degraded or polymerized due to storage.

The high concentration in the mixture of 50 mM PEG and APTS improves bimolecular reaction speed. This allows preparation of the reagent without unwanted decay. A higher concentration of NHS over APTS helps to drive the reaction of APTS with NHS groups to completion. The capillary gap increases the speed of surface reaction by eliminating diffusion limitation. Because there are substantially no gradients in the mixture, treatment of the surfaces 20 is more homogeneous. The larger the surface to volume ratio between the surfaces 20, the more polymerization reactions are reduced and reaction of triethoxysilane with the surfaces 20 is favored. These may otherwise reduce the specificity of detection schemes such as detection of primary amines through CBQCA or NHS-rhodamine. A low level of APTS present in the mixture significantly reduces the background level against which primary amines are detected.

Reaction of the reagent between the surfaces 20 is stopped by removal of the solution by filter paper followed by three wash cycles with DMSO. Washing removes unreacted heterobifunctional molecules together with polymerization products and homobifuctional byproducts. The surfaces 20 are then disassembled and blow dried with nitrogen to remove traces of DMSO. Capture molecules 10 are then attached to the freshly NHS-activated surfaces 20. Alternatively, the surfaces 20 may be stored for a few days in dry argon.

Treated glass surfaces 20 as herein before described can anchor oligonucleotides with terminal aminogroups (5' or 3' end), proteins, and other $NH_2$-functionalized molecules. In a particularly preferred embodiment of the present invention, chemisorption is performed by filling a PDMS microfluidic network applied to the NHS-activated surface 20 with aqueous solutions of amino-functionalized compounds. Oligonucleotides are chemisorbed to the surface 20 in an aqueous solution containing 10% DMSO and 15–20% PEG (MW=1000). A concentration of 20 mM oligonucleotide provides particularly homogeneous coverage of the surface 20 by oligonucleotides during chemical reaction and remains substantially unaffected by drying.

Figure 5A:
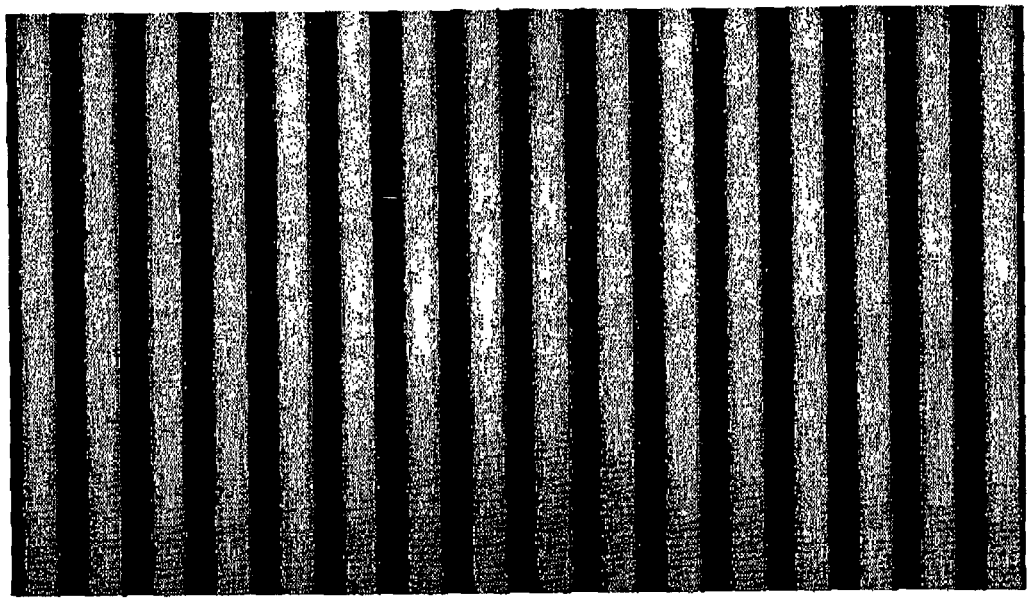
FIG. 5A is a photographic image of a treated surface.
Figure 5B:
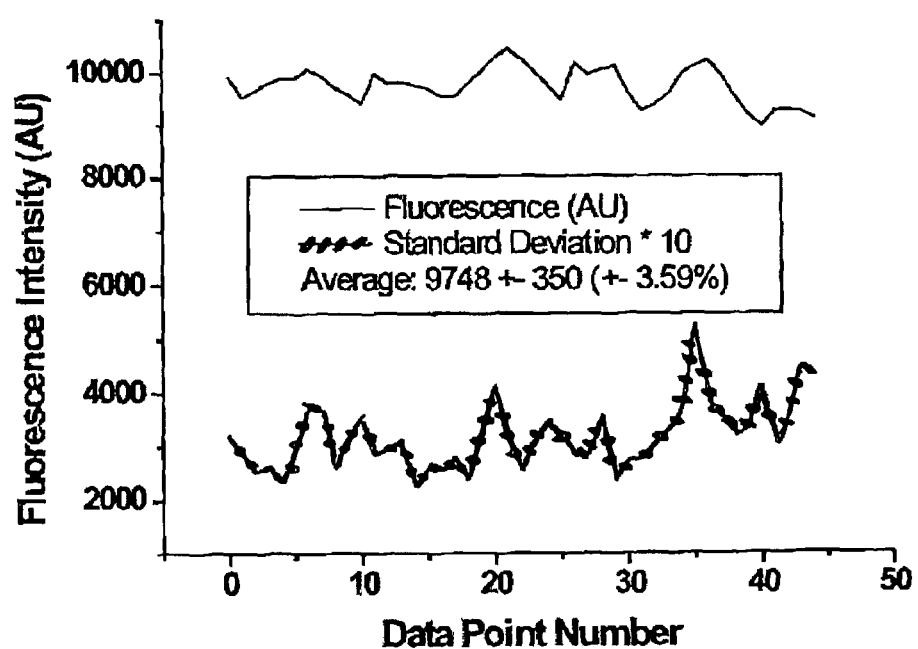
FIG. 5B is a plot of fluorescence versus data point corresponding to the surface of FIG. 5A.

FIGS. 5A to 5D exemplify improved homogeneity achievable using surface functionalization embodying the present invention. FIG. 5A shows a fluorescence image of patterned TAMRA labelled 18-mer DNA oligomer molecules chemisorbed to the surface by an NHS-PEG-APTS conjugate spacer. The lighter stripes show the chemisorbed oligomer molecules. FIG. 5B is a plot of fluorescence counts from the FIG. 5A surface showing an intraspot standard deviation <2% and an interspot standard deviation <4%. The fluorescence intensity averaged over 45 separate areas distributed over the image in this case is 9748+−350 counts. The variability is less than 4%. For one area, 600 pixels were averaged. The accuracy of patterning remains stable even during washing and hybridization cycles.

Figure 5C:
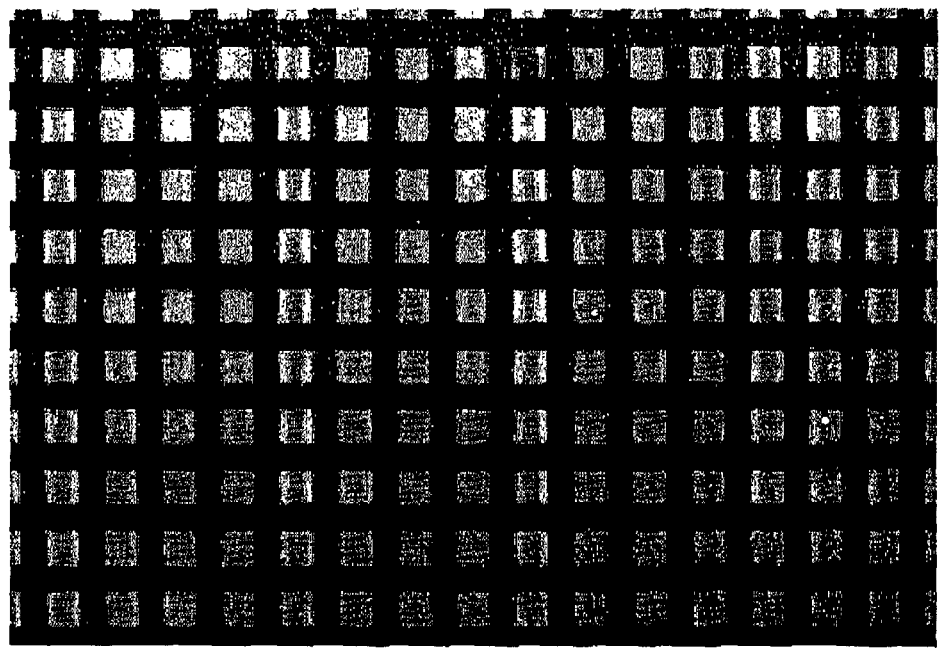
FIG. 5C is a photographic image of another treated surface.
Figure 5D:
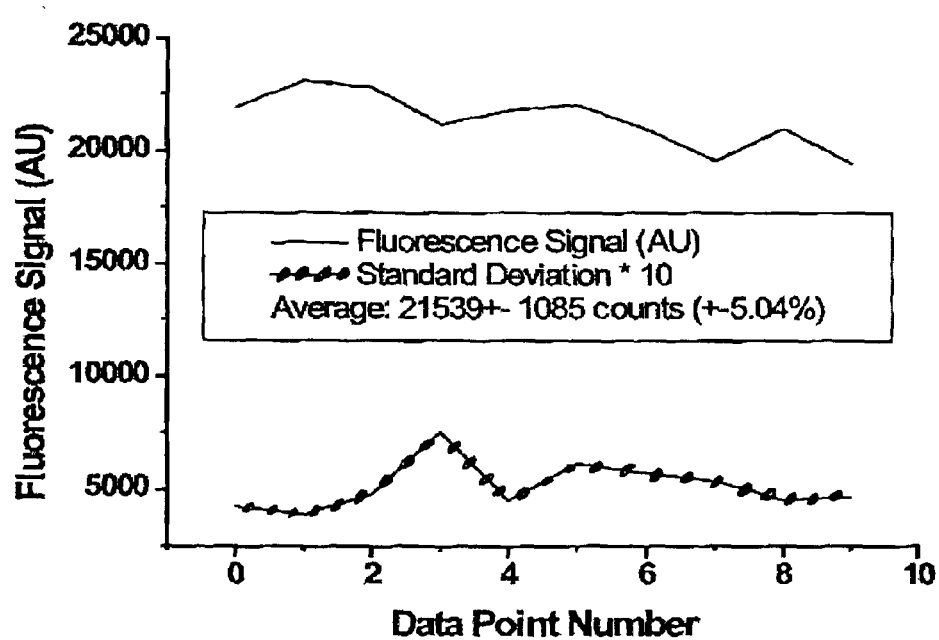
FIG. 5D is a plot of fluorescence versus data point corresponding to the surface of FIG. 5B.

Referring to FIGS. 5C and 5D, this is demonstrated by the image and graph therein. The lighter square areas are created by patterned chemisorption of aptamers along vertical tracks and by patterned hybridization of labelled 16-mer oligomer primers along spaced horizontal tracks. The fluorescence image averaged over 9 areas is 21539+−1085 counts. The variability is 5%. For one area, 784 pixels were averaged.

Preferred embodiments of the present invention have been described herein by way of example only. It will be appreciated by those skilled in the art that there are many more embodiments of the present invention possible.

The invention claimed is:

1. A process for producing a biomolecular monolayer on a surface, comprising:

reacting homobifunctional polyethylene glycol (PEG) N-hydroxy succinimide (NHS) with aminopropyl trimethoxysilane at between 46 and 50 degrees Celsius for between 30 and 60 minutes to form a NHS-PEG-triethoxysilane reagent, wherein the aminopropyl trimethoxysilane comprises a first functional group for forming a covalent bond to a surface group and a second functional group for forming a covalent bond with the homobifunctional PEG NHS;

exposing the surface to the NHS-PEG-triethoxysilane reagent to form the covalent bond between the surface and first functional groups and obtain a self-assembled monolayer; and thereafter reacting the monolayer with biomolecules.

2. The process of claim 1, wherein reacting the homobifunctional PEG NHS and the aminopropyl trimethoxysilane occurs in a solution of dimethyl sulphoxide.

* * * * *